United States Patent
Donohue

(10) Patent No.: US 9,632,103 B2
(45) Date of Patent: Apr. 25, 2017

(54) LINEAR TRACK DIAGNOSTIC ANALYZER

(71) Applicant: Abbott Laboratories, Abbott Park, IL (US)

(72) Inventor: Joseph P. Donohue, Pleasant Prairie, WI (US)

(73) Assignee: Abbott Laboraties, Abbott Park, IL (US)

( * ) Notice: Subject to any disclaimer, the term of this patent is extended or adjusted under 35 U.S.C. 154(b) by 392 days.

(21) Appl. No.: 14/213,847

(22) Filed: Mar. 14, 2014

(65) Prior Publication Data
US 2014/0287523 A1 Sep. 25, 2014

Related U.S. Application Data

(60) Provisional application No. 61/790,599, filed on Mar. 15, 2013.

(51) Int. Cl.
*G01N 35/04* (2006.01)
*G01N 35/02* (2006.01)

(52) U.S. Cl.
CPC ........... *G01N 35/04* (2013.01); *G01N 35/021* (2013.01); *G01N 35/026* (2013.01);
(Continued)

(58) Field of Classification Search
CPC .................................................... G01N 35/04
(Continued)

(56) References Cited

U.S. PATENT DOCUMENTS 2,725,971 A  12/1955 Clark-Riede
2,770,352 A  11/1956 Moller
(Continued)

FOREIGN PATENT DOCUMENTS

CA  2254017  5/2000
CA  2497397  2/2004
(Continued)

OTHER PUBLICATIONS

International Search Report and Written Opinion, dated Aug. 11, 2014, 11 pages.

*Primary Examiner* — Christine T Mui
*Assistant Examiner* — Emily Berkeley
(74) *Attorney, Agent, or Firm* — Klintworth & Rozenblat IP LLC

(57) ABSTRACT

A diagnostic analyzer system includes a linear track, at least one pipetting device, and at least one diagnostic module. The linear track includes a pre-treatment lane disposed parallel to at least one processing lane. The linear track moves reaction vessels, containing samples, held by the pre-treatment lane and by the at least one processing lane. The pre-treatment lane pre-treats the samples in the reaction vessels of the pre-treatment lane. The pre-treatment lane is not connected to any diagnostic module for testing the samples in the reaction vessels of the pre-treatment lane. The at least one pipetting device transfers the pre-treated samples from the reaction vessels in the pre-treatment lane to the reaction vessels in the at least one processing lane. The at least one diagnostic module is connected to the at least one processing lane for testing the pre-treated samples transferred into the reaction vessels in the at least one processing lane.

9 Claims, 6 Drawing Sheets

(52) U.S. Cl.
CPC ............. *G01N 2035/0408* (2013.01); *G01N 2035/0465* (2013.01); *Y10T 436/11* (2015.01); *Y10T 436/113332* (2015.01); *Y10T 436/25* (2015.01); *Y10T 436/2575* (2015.01)

(58) Field of Classification Search
USPC ...................................................... 436/180
See application file for complete search history.

(56) References Cited

U.S. PATENT DOCUMENTS

| | | |
|---|---|---|
| 2,807,350 A | 9/1957 | Black, Jr. |
| 2,891,668 A | 6/1959 | Hunt |
| 3,143,201 A | 8/1964 | Wyle |
| 3,350,946 A | 11/1967 | Isreeli |
| 3,432,271 A | 3/1969 | Wasilewski |
| 3,481,709 A | 12/1969 | Slone |
| 3,511,613 A | 5/1970 | Jones |
| 3,532,469 A | 10/1970 | Vicario |
| 3,536,449 A | 10/1970 | Astle |
| 3,622,279 A | 11/1971 | Moran |
| 3,623,515 A | 11/1971 | Gilson |
| 3,635,394 A | 1/1972 | Natelson |
| 3,644,095 A | 2/1972 | Bechtler |
| 3,660,638 A | 5/1972 | Oberli |
| 3,687,632 A | 8/1972 | Natelson |
| 3,716,338 A | 2/1973 | Moran |
| 3,722,790 A | 3/1973 | Natelson |
| 3,723,066 A | 3/1973 | Moran |
| 3,728,079 A | 4/1973 | Moran |
| 3,728,080 A | 4/1973 | Moran |
| 3,762,879 A | 10/1973 | Moran |
| 3,785,773 A | 1/1974 | Rohrbaugh |
| 3,825,410 A | 7/1974 | Bagshawe |
| 3,826,622 A | 7/1974 | Natelson |
| 3,841,838 A | 10/1974 | Natelson |
| 3,882,619 A | 5/1975 | Durand |
| 3,888,629 A | 6/1975 | Bagshawe |
| 3,897,216 A | 7/1975 | Jones |
| 3,932,131 A | 1/1976 | Rolfo-Fontana |
| 3,985,508 A | 10/1976 | Williams |
| 3,994,594 A | 11/1976 | Sandrock |
| 4,039,288 A | 8/1977 | Moran |
| 4,055,396 A | 10/1977 | Meyer |
| 4,140,018 A | 2/1979 | Maldarelli |
| 4,158,545 A | 6/1979 | Yamashita et al. |
| 4,168,955 A | 9/1979 | Allington |
| 4,190,420 A | 2/1980 | Covington |
| 4,244,459 A | 1/1981 | Garrett |
| 4,251,159 A | 2/1981 | White |
| 4,260,581 A | 4/1981 | Sakurada |
| 4,278,437 A | 7/1981 | Haggar |
| 4,315,891 A | 2/1982 | Sakurada |
| 4,363,781 A | 12/1982 | Akamatsu |
| 4,363,782 A | 12/1982 | Yamashita |
| 4,366,119 A | 12/1982 | Takeuchi |
| 4,413,534 A | 11/1983 | Tomoff |
| 4,459,864 A | 7/1984 | Cirincione |
| 4,495,149 A | 1/1985 | Iwata |
| 4,527,438 A | 7/1985 | Fosslien |
| 4,537,231 A | 8/1985 | Hasskamp |
| 4,600,120 A | 7/1986 | Sabo |
| 4,609,017 A | 9/1986 | Coulter |
| 4,623,008 A | 11/1986 | Shibata |
| 4,634,575 A | 1/1987 | Kawakami |
| 4,664,885 A | 5/1987 | Minekane et al. |
| 4,678,752 A | 7/1987 | Thorne |
| 4,692,308 A | 9/1987 | Riley et al. |
| 4,694,951 A | 9/1987 | Gibbemeyer |
| 4,713,219 A | 12/1987 | Gerken |
| 4,718,319 A | 1/1988 | Bajohr |
| 4,719,087 A | 1/1988 | Hanaway |
| 4,720,463 A | 1/1988 | Farber |
| 4,731,225 A | 3/1988 | Wakatake |
| 4,751,186 A | 6/1988 | Baisch |
| 4,797,258 A | 1/1989 | Mochida |
| 4,815,625 A | 3/1989 | Filhol |
| 4,818,883 A | 4/1989 | Anderson |
| 4,853,188 A | 8/1989 | Toya |
| 4,855,110 A | 8/1989 | Marker, Jr. |
| 4,861,553 A | 8/1989 | Mawhirt |
| 4,861,554 A | 8/1989 | Sakuma |
| 4,900,513 A | 2/1990 | Barker |
| 4,931,256 A | 6/1990 | Mack et al. |
| 4,935,274 A | 6/1990 | DeBenedictis |
| 4,948,564 A | 8/1990 | Root |
| 4,970,053 A | 11/1990 | Fechtner |
| 5,005,721 A | 4/1991 | Jordan |
| 5,008,082 A | 4/1991 | Shaw |
| 5,009,942 A | 4/1991 | Benin |
| 5,035,861 A | 7/1991 | Grandone |
| 5,035,866 A | 7/1991 | Wannlund |
| 5,055,263 A | 10/1991 | Meltzer |
| 5,075,082 A | 12/1991 | Fechtner |
| 5,098,661 A | 3/1992 | Anderson |
| 5,112,574 A | 5/1992 | Horton |
| 5,125,680 A | 6/1992 | Bejean |
| 5,128,104 A | 7/1992 | Murphy |
| 5,145,646 A | 9/1992 | Tyranski |
| 5,158,895 A | 10/1992 | Ashihara |
| 5,173,741 A | 12/1992 | Wakatake |
| 5,178,834 A | 1/1993 | Kagayama et al. |
| 5,242,659 A | 9/1993 | Wurschum |
| 5,244,633 A | 9/1993 | Jakubowicz |
| 5,250,440 A | 10/1993 | Kelln |
| 5,265,655 A | 11/1993 | Hirsch |
| 5,270,011 A | 12/1993 | Altherr |
| 5,271,899 A | 12/1993 | Carbonari |
| 5,277,871 A | 1/1994 | Fujii |
| 5,290,708 A | 3/1994 | Ashihara |
| 5,306,510 A | 4/1994 | Meltzer |
| 5,316,726 A | 5/1994 | Babson |
| 5,322,668 A | 6/1994 | Tomasso |
| 5,332,549 A | 7/1994 | MacIndoe, Jr. |
| 5,364,592 A | 11/1994 | Lewis |
| 5,368,820 A | 11/1994 | Lautenschlager |
| 5,374,395 A * | 12/1994 | Robinson ............. G01N 21/253 422/562 |
| 5,380,487 A | 1/1995 | Choperena |
| 5,380,488 A | 1/1995 | Wakatake |
| 5,422,075 A | 6/1995 | Aoki |
| 5,424,036 A | 6/1995 | Ushikubo |
| 5,445,794 A | 8/1995 | Wihlborg |
| 5,456,884 A | 10/1995 | Lewis |
| 5,482,839 A | 1/1996 | Ashihara et al. |
| 5,482,863 A | 1/1996 | Knobel |
| 5,507,410 A | 4/1996 | Clark |
| 5,511,690 A | 4/1996 | Calhoun |
| 5,518,688 A | 5/1996 | Gianino |
| 5,544,778 A | 8/1996 | Goncalves |
| 5,554,536 A | 9/1996 | Rising |
| 5,567,386 A | 10/1996 | Markin |
| 5,578,272 A | 11/1996 | Koch |
| 5,580,524 A | 12/1996 | Forrest |
| 5,582,796 A | 12/1996 | Carey |
| 5,605,665 A | 2/1997 | Clark |
| 5,623,415 A | 4/1997 | O'Bryan et al. |
| 5,628,428 A | 5/1997 | Calhoun |
| 5,632,396 A | 5/1997 | Burns |
| 5,637,275 A | 6/1997 | Carey |
| 5,645,800 A | 7/1997 | Masterson |
| 5,650,125 A | 7/1997 | Bosanquet |
| 5,653,940 A | 8/1997 | Carey |
| 5,658,799 A | 8/1997 | Choperena |
| 5,670,117 A | 9/1997 | Erb |
| 5,672,317 A | 9/1997 | Buhler |
| 5,679,948 A | 10/1997 | Carey |
| 5,683,659 A | 11/1997 | Hovatter |
| 5,693,292 A | 12/1997 | Choperena |
| 5,700,429 A | 12/1997 | Buhler |
| 5,720,377 A | 2/1998 | Lapeus et al. |
| 5,720,406 A | 2/1998 | Fassbind |
| 5,736,101 A | 4/1998 | Gianino |
| 5,741,708 A | 4/1998 | Carey |

(56) References Cited

U.S. PATENT DOCUMENTS

| | | |
|---|---|---|
| 5,753,186 A | 5/1998 | Hanley |
| 5,766,549 A | 6/1998 | Gao et al. |
| 5,772,962 A | 6/1998 | Uchida et al. |
| 5,788,928 A | 8/1998 | Carey |
| 5,800,784 A | 9/1998 | Horn |
| 5,814,276 A | 9/1998 | Riggs |
| 5,846,491 A | 12/1998 | Choperena |
| 5,849,247 A | 12/1998 | Uzan |
| 5,863,506 A | 1/1999 | Farren |
| 5,876,670 A | 3/1999 | Mitsumaki et al. |
| 5,885,529 A | 3/1999 | Babson |
| 5,885,530 A | 3/1999 | Babson |
| 5,888,825 A | 3/1999 | Carr et al. |
| 5,902,549 A | 5/1999 | Mimura et al. |
| 5,922,289 A | 7/1999 | Wong |
| 5,931,828 A | 8/1999 | Durkee |
| 5,945,071 A | 8/1999 | Ekiriwang |
| 5,952,218 A | 9/1999 | Lee |
| 5,957,264 A | 9/1999 | Carey |
| 5,959,221 A | 9/1999 | Boyd |
| RE36,341 E | 10/1999 | Howell |
| 5,963,368 A | 10/1999 | Domanik |
| 5,966,309 A | 10/1999 | O'Bryan et al. |
| 5,968,453 A | 10/1999 | Shugart |
| 5,972,295 A | 10/1999 | Hanawa et al. |
| 5,985,214 A | 11/1999 | Beckey |
| 5,985,218 A | 11/1999 | Goodale |
| 5,988,236 A | 11/1999 | Fawcett |
| 6,019,945 A | 2/2000 | Ohishi et al. |
| 6,024,204 A | 2/2000 | van Dyke, Jr. |
| 6,030,582 A | 2/2000 | Levy |
| 6,056,106 A | 5/2000 | Van Dyke, Jr. |
| 6,063,340 A | 5/2000 | Lewis et al. |
| 6,063,341 A | 5/2000 | Fassbind |
| 6,074,615 A | 6/2000 | Lewis |
| 6,074,617 A | 6/2000 | DeYoung et al. |
| 6,081,326 A | 6/2000 | Gelin |
| 6,117,391 A | 9/2000 | Bakonyi |
| 6,117,392 A | 9/2000 | Hanawa |
| 6,117,683 A | 9/2000 | Kodama |
| 6,136,273 A | 10/2000 | Banar |
| 6,146,882 A | 11/2000 | Uematsu |
| 6,149,872 A | 11/2000 | Mack et al. |
| 6,202,829 B1 | 3/2001 | van Dyke, Jr. et al. |
| 6,204,764 B1 | 3/2001 | Maloney |
| 6,220,451 B1 | 4/2001 | Hoffmann |
| 6,254,826 B1 | 7/2001 | Acosta |
| 6,265,225 B1 | 7/2001 | Otto |
| 6,274,374 B1 | 8/2001 | Astle |
| 6,299,567 B1 | 10/2001 | Forrest et al. |
| 6,325,129 B1 | 12/2001 | Wright |
| 6,335,166 B1 | 1/2002 | Ammann |
| 6,337,053 B1 | 1/2002 | Tajima |
| 6,355,488 B1 | 3/2002 | Rousseau |
| 6,358,472 B1 | 3/2002 | DeYoung |
| 6,361,744 B1 | 3/2002 | Levy |
| 6,368,561 B1 | 4/2002 | Rutishauser |
| 6,368,872 B1 | 4/2002 | Juranas |
| 6,374,989 B1 | 4/2002 | van Dyke, Jr. |
| 6,379,625 B1 | 4/2002 | Zuk, Jr. |
| 6,403,035 B1 | 6/2002 | Caratsch |
| 6,413,780 B1 | 7/2002 | Bach |
| 6,436,349 B1 | 8/2002 | Carey et al. |
| 6,440,368 B1 | 8/2002 | Cohen |
| 6,440,371 B1 | 8/2002 | Dumitrescu |
| 6,458,324 B1 | 10/2002 | Schinzel |
| 6,461,570 B2 | 10/2002 | Ishihara |
| 6,468,800 B1 | 10/2002 | Stylli |
| 6,472,218 B1 | 10/2002 | Stylli |
| 6,489,169 B1 | 12/2002 | Cohen |
| 6,498,037 B1 | 12/2002 | Carey et al. |
| 6,511,634 B1 | 1/2003 | Bradshaw et al. |
| 6,517,780 B1 | 2/2003 | Cortelazzo |
| 6,517,782 B1 | 2/2003 | Horner |
| 6,521,183 B1 | 2/2003 | Burri |
| 6,555,062 B1 | 4/2003 | Lewis et al. |
| 6,588,625 B2 | 7/2003 | Luoma, II et al. |
| 6,599,476 B1 | 7/2003 | Watson |
| 6,599,749 B1 | 7/2003 | Kodama et al. |
| 6,605,213 B1 | 8/2003 | Ammann |
| 6,673,595 B2 | 1/2004 | Barbera-Guillem |
| 6,677,857 B2 | 1/2004 | Bara et al. |
| 6,678,577 B1 | 1/2004 | Stylli |
| 6,685,884 B2 | 2/2004 | Stylli |
| 6,696,298 B2 | 2/2004 | Cook |
| 6,709,634 B1 | 3/2004 | Okada |
| 6,733,728 B1 | 5/2004 | Mimura |
| 6,746,648 B1 | 6/2004 | Mattila |
| 6,752,965 B2 | 6/2004 | Levy |
| 6,752,967 B2 | 6/2004 | Farina |
| 6,764,649 B2 | 7/2004 | Ammann |
| 6,776,964 B1 | 8/2004 | Wijnschenk |
| 6,790,412 B2 | 9/2004 | Willenbring |
| 6,790,413 B2 | 9/2004 | Ngo |
| 6,793,888 B2 | 9/2004 | Qureshi |
| 6,799,696 B2 | 10/2004 | Okada |
| 6,808,304 B2 | 10/2004 | Gebrian |
| 6,818,060 B2 | 11/2004 | Stewart |
| 6,827,902 B1 | 12/2004 | Kuriyama |
| 6,829,954 B2 | 12/2004 | Katagi |
| 6,843,357 B2 | 1/2005 | Bybee |
| 6,843,962 B2 | 1/2005 | Haslam |
| 6,846,456 B2 | 1/2005 | Acosta |
| 6,852,283 B2 | 2/2005 | Acosta |
| 6,878,343 B2 | 4/2005 | Sklar |
| 6,881,380 B1 | 4/2005 | Mootz |
| 6,890,485 B1 | 5/2005 | Stylli |
| 6,890,742 B2 | 5/2005 | Ammann |
| 6,893,611 B1 | 5/2005 | Cohen |
| 6,896,120 B2 | 5/2005 | Barry |
| 6,896,849 B2 | 5/2005 | Reed |
| 6,899,850 B2 | 5/2005 | Haywood |
| 6,939,513 B2 | 9/2005 | Berray |
| 6,948,389 B2 | 9/2005 | Brinker |
| 6,951,545 B2 | 10/2005 | Smith |
| 6,977,722 B2 | 12/2005 | Wohlstadter |
| 6,998,094 B2 | 2/2006 | Haslam |
| 6,999,847 B2 | 2/2006 | Barry et al. |
| 7,011,792 B2 | 3/2006 | Mimura |
| 7,028,831 B2 | 4/2006 | Veiner |
| 7,029,922 B2 | 4/2006 | Miller |
| 7,033,820 B2 | 4/2006 | Ammann |
| 7,067,323 B2 | 6/2006 | Veale et al. |
| 7,070,053 B1 | 7/2006 | Abrams |
| 7,091,864 B2 | 8/2006 | Veitch et al. |
| 7,112,303 B2 | 9/2006 | Itoh |
| 7,118,892 B2 | 10/2006 | Ammann |
| 7,125,722 B2 | 10/2006 | Safar |
| 7,135,145 B2 | 11/2006 | Ammann |
| 7,141,213 B1 | 11/2006 | Pang |
| 7,168,390 B2 | 1/2007 | Gudmundsson |
| 7,168,391 B2 | 1/2007 | Gudmundsson |
| 7,169,356 B2 | 1/2007 | Gebrian |
| 7,182,912 B2 | 2/2007 | Carey |
| 7,187,286 B2 | 3/2007 | Morris et al. |
| 7,199,712 B2 | 4/2007 | Tafas |
| 7,219,800 B2 | 5/2007 | Bülow |
| 7,220,385 B2 | 5/2007 | Blecka |
| 7,233,838 B2 | 6/2007 | Barry |
| 7,250,303 B2 | 7/2007 | Jakubowicz |
| 7,264,111 B2 | 9/2007 | Veiner |
| 7,267,795 B2 | 9/2007 | Ammann |
| 7,270,229 B2 | 9/2007 | Perazzo |
| 7,291,309 B2 | 11/2007 | Watson |
| 7,294,312 B2 | 11/2007 | Green |
| 7,299,981 B2 | 11/2007 | Hickle |
| 7,300,628 B2 | 11/2007 | Nogawa |
| 7,306,767 B2 | 12/2007 | Mathus |
| 7,309,469 B2 | 12/2007 | Anderson |
| 7,331,474 B2 | 2/2008 | Veiner |
| 7,338,635 B2 | 3/2008 | Miyake |
| 7,338,803 B2 | 3/2008 | Mizzer |
| 7,361,305 B2 | 4/2008 | Mimura |
| 7,380,654 B2 | 6/2008 | Barry |

(56) References Cited

U.S. PATENT DOCUMENTS

| | | |
|---|---|---|
| 7,382,258 B2 | 6/2008 | Oldham et al. |
| 7,384,600 B2 | 6/2008 | Burns |
| 7,396,509 B2 | 7/2008 | Burns |
| 7,400,983 B2 | 7/2008 | Feingold |
| 7,402,282 B2 | 7/2008 | LaCourt |
| 7,407,627 B1 | 8/2008 | Rosenberg |
| 7,411,508 B2 | 8/2008 | Harazin et al. |
| 7,448,487 B2 | 11/2008 | Koike |
| 7,458,483 B2 | 12/2008 | Luoma, II |
| 7,482,143 B2 | 1/2009 | Ammann |
| 7,488,453 B2 | 2/2009 | Takahashi |
| 7,491,364 B2 | 2/2009 | Mattila |
| 7,501,094 B2 | 3/2009 | Bysouth |
| 7,504,067 B2 | 3/2009 | Itoh |
| 7,510,683 B2 | 3/2009 | Itoh |
| 7,513,127 B2 | 4/2009 | Owen |
| 7,524,652 B2 | 4/2009 | Ammann |
| 7,526,968 B2 | 5/2009 | Lisec |
| 7,560,255 B2 | 7/2009 | Ammann |
| 7,560,256 B2 | 7/2009 | Ammann |
| 7,572,638 B2 | 8/2009 | Pressman |
| 7,625,748 B2 | 12/2009 | Ogura |
| 7,628,954 B2 | 12/2009 | Gomm |
| 7,638,337 B2 | 12/2009 | Ammann |
| 7,639,139 B2 | 12/2009 | Tafas |
| 7,641,855 B2 | 1/2010 | Farina |
| 7,662,339 B2 | 2/2010 | Mattila |
| 7,663,487 B2 | 2/2010 | Morris et al. |
| 7,666,602 B2 | 2/2010 | Ammann |
| 7,666,681 B2 | 2/2010 | Ammann |
| 7,667,603 B2 | 2/2010 | Bolander |
| 7,670,553 B2 | 3/2010 | Babson |
| 7,687,034 B2 | 3/2010 | Dumitrescu |
| 7,688,207 B2 | 3/2010 | Fritchie |
| 7,692,530 B2 | 4/2010 | Turner et al. |
| 7,700,043 B2 | 4/2010 | Mimura |
| 7,718,072 B2 | 5/2010 | Safar |
| 7,731,898 B2 | 6/2010 | Burkhardt |
| 7,754,149 B2 | 7/2010 | Sugiyama |
| 7,785,299 B2 | 8/2010 | Crawford |
| 7,790,108 B2 | 9/2010 | Müller |
| 7,818,132 B2 | 10/2010 | Pritchard |
| 7,842,504 B2 | 11/2010 | Devlin, Sr. |
| 7,846,384 B2 | 12/2010 | Watson |
| 7,850,912 B2 | 12/2010 | Favuzzi |
| 7,850,914 B2 | 12/2010 | Veiner et al. |
| 7,854,892 B2 | 12/2010 | Veiner et al. |
| 7,855,084 B2 | 12/2010 | Jakubowicz |
| 7,858,032 B2 | 12/2010 | Le Comte |
| 7,858,033 B2 | 12/2010 | Itoh |
| 7,866,464 B2 | 1/2011 | Miyatani et al. |
| 7,867,768 B2 | 1/2011 | Ryan |
| 7,875,245 B2 | 1/2011 | Favuzzi |
| 7,879,290 B2 | 2/2011 | Noda |
| 7,880,617 B2 | 2/2011 | Morris et al. |
| 7,901,624 B2 | 3/2011 | Hansen |
| 7,914,737 B2 | 3/2011 | Baumann |
| 7,922,986 B2 | 4/2011 | Byrnard |
| 7,931,861 B2 | 4/2011 | Kitagawa |
| 7,931,879 B2 | 4/2011 | D'Amore |
| 7,932,826 B2 | 4/2011 | Fritchie |
| 7,939,020 B2 | 5/2011 | Nogawa |
| 7,943,100 B2 | 5/2011 | Rousseau |
| 7,947,512 B2 | 5/2011 | Tajima |
| 7,975,852 B2 | 7/2011 | Charpentier |
| 7,976,794 B2 | 7/2011 | Trump |
| 7,985,375 B2 | 7/2011 | Edens |
| 7,998,409 B2 | 8/2011 | Veiner |
| 8,017,093 B2 | 9/2011 | Mattila |
| 8,017,094 B2 | 9/2011 | Meyer |
| 8,029,746 B2 | 10/2011 | Yu |
| 8,035,485 B2 | 10/2011 | Fritchie |
| 8,038,941 B2 | 10/2011 | Devlin |
| 8,012,419 B2 | 11/2011 | Eby |
| 8,049,623 B2 | 11/2011 | Morris et al. |
| 8,080,204 B2 | 12/2011 | Ryan |
| 8,211,301 B2 | 7/2012 | Safar |
| 8,252,232 B2 | 8/2012 | Neeper |
| 8,361,387 B2 | 1/2013 | Schacher |
| 8,361,396 B2 | 1/2013 | Parker |
| 8,435,738 B2 | 5/2013 | Holmes |
| 8,492,155 B2 | 7/2013 | Bunce |
| 2001/0019826 A1 | 9/2001 | Ammann |
| 2001/0041336 A1 | 11/2001 | Anderson et al. |
| 2002/0028489 A1 | 3/2002 | Ammann |
| 2002/0085959 A1 | 7/2002 | Carey |
| 2002/0098117 A1 | 7/2002 | Ammann |
| 2002/0127727 A1 | 9/2002 | Bach |
| 2002/0137194 A1 | 9/2002 | Ammann |
| 2002/0137197 A1 | 9/2002 | Ammann |
| 2002/0164807 A1 | 11/2002 | Itaya |
| 2003/0027206 A1 | 2/2003 | Ammann |
| 2003/0047418 A1 | 3/2003 | Okada |
| 2003/0049170 A1 | 3/2003 | Tamura et al. |
| 2003/0054542 A1 | 3/2003 | Burns |
| 2003/0155321 A1 | 8/2003 | Bauer et al. |
| 2003/0194349 A1 | 10/2003 | Carey |
| 2003/0215357 A1 | 11/2003 | Leeker |
| 2003/0224524 A1 | 12/2003 | Arai et al. |
| 2004/0022682 A1 | 2/2004 | Itoh |
| 2004/0035816 A1 | 2/2004 | Okiyama |
| 2004/0042339 A1 | 3/2004 | Gebrian et al. |
| 2004/0094385 A1 | 5/2004 | Bybee |
| 2004/0096362 A1 | 5/2004 | Barry et al. |
| 2004/0115796 A1 | 6/2004 | Burns |
| 2004/0136869 A1 | 7/2004 | Itoh |
| 2004/0141882 A1 | 7/2004 | Mimura |
| 2004/0163931 A1 | 8/2004 | Barry et al. |
| 2004/0266015 A1 | 12/2004 | Favuzzi |
| 2005/0023109 A1 | 2/2005 | Barry |
| 2005/0042138 A1 | 2/2005 | Ueda |
| 2005/0084974 A1 | 4/2005 | Veale |
| 2005/0130198 A1 | 6/2005 | Ammann |
| 2005/0194237 A1 | 9/2005 | Veiner |
| 2005/0194333 A1 | 9/2005 | Veiner |
| 2005/0196320 A1 | 9/2005 | Veiner et al. |
| 2005/0233370 A1 | 10/2005 | Ammann |
| 2005/0239127 A1 | 10/2005 | Ammann |
| 2005/0258018 A1 | 11/2005 | Barry |
| 2005/0266489 A1 | 12/2005 | Ammann |
| 2005/0266570 A1 | 12/2005 | Carey |
| 2006/0003373 A1 | 1/2006 | Ammann |
| 2006/0013729 A1 | 1/2006 | Carey |
| 2006/0110288 A1 | 5/2006 | Mimura |
| 2006/0177346 A1 | 8/2006 | Veiner |
| 2006/0190185 A1 | 8/2006 | Ford et al. |
| 2006/0216199 A1 | 9/2006 | Koike |
| 2006/0258010 A1 | 11/2006 | Safar |
| 2006/0275906 A1 | 12/2006 | Devlin |
| 2007/0077172 A1 | 4/2007 | Sugiyama |
| 2007/0207056 A1 | 9/2007 | Veiner |
| 2007/0225857 A1 | 9/2007 | Barry |
| 2007/0255756 A1 | 11/2007 | Satomura et al. |
| 2008/0008624 A1 | 1/2008 | Veiner |
| 2008/0020467 A1 | 1/2008 | Barnes |
| 2008/0044260 A1 | 2/2008 | Miyatani |
| 2008/0063563 A1 | 3/2008 | Watari |
| 2008/0063573 A1 | 3/2008 | Ammann |
| 2008/0069730 A1 | 3/2008 | Itoh |
| 2008/0089818 A1 | 4/2008 | Ammann |
| 2008/0096214 A1 | 4/2008 | Ammann |
| 2008/0102527 A1 | 5/2008 | Ammann |
| 2008/0181817 A1 | 7/2008 | Mimura |
| 2008/0190735 A1 | 8/2008 | Luoma |
| 2008/0212400 A1 | 9/2008 | Ammann |
| 2008/0226498 A1 | 9/2008 | Stylli |
| 2008/0226509 A1 | 9/2008 | Sattler |
| 2008/0241837 A1 | 10/2008 | Ammann |
| 2008/0268528 A1 | 10/2008 | Ammann |
| 2008/0299007 A1 | 12/2008 | Noguchi |
| 2009/0029352 A1 | 1/2009 | Ammann |
| 2009/0029871 A1 | 1/2009 | Ammann |
| 2009/0029877 A1 | 1/2009 | Ammann |
| 2009/0058617 A1 | 3/2009 | Wu |

(56) References Cited

U.S. PATENT DOCUMENTS

| | | | |
|---|---|---|---|
| 2009/0074616 A1 | 3/2009 | Sento | |
| 2009/0130749 A1 | 5/2009 | Ammann | |
| 2009/0134978 A1 | 5/2009 | Imai | |
| 2009/0155123 A1* | 6/2009 | Williams | ............... B01L 3/021 422/65 |
| 2009/0160654 A1 | 6/2009 | Yang | |
| 2009/0162247 A1 | 6/2009 | Tokieda | |
| 2009/0325274 A1 | 12/2009 | Hamada | |
| 2010/0001854 A1 | 1/2010 | Kojima | |
| 2010/0001876 A1 | 1/2010 | Sasaki | |
| 2010/0007501 A1 | 1/2010 | Yang | |
| 2010/0013595 A1 | 1/2010 | Torre-Bueno | |
| 2010/0021993 A1 | 1/2010 | Wang | |
| 2010/0028124 A1 | 2/2010 | Lackner | |
| 2010/0034701 A1 | 2/2010 | Pedrazzini | |
| 2010/0075430 A1 | 3/2010 | Hofstadler | |
| 2010/0112703 A1 | 3/2010 | Farrar | |
| 2010/0093097 A1 | 4/2010 | Kawamura | |
| 2010/0097231 A1 | 4/2010 | Elsenhans | |
| 2010/0122586 A1 | 5/2010 | Misu | |
| 2010/0124518 A1 | 5/2010 | Koike | |
| 2010/0166605 A1 | 7/2010 | Hamada | |
| 2010/0166615 A1 | 7/2010 | Mattila | |
| 2010/0188244 A1 | 7/2010 | Sattler et al. | |
| 2010/0191382 A1 | 7/2010 | Samuhel | |
| 2010/0248213 A1 | 9/2010 | Feiglin | |
| 2010/0282003 A1 | 11/2010 | Hamada | |
| 2010/0300831 A1 | 12/2010 | Pedrazzini | |
| 2010/0314216 A1 | 12/2010 | Lanfranchi | |
| 2011/0001609 A1 | 1/2011 | Oldham et al. | |
| 2011/0027150 A1 | 2/2011 | Tuffet | |
| 2011/0064543 A1 | 3/2011 | Nuotio | |
| 2011/0076193 A1 | 3/2011 | Kitagawa | |
| 2011/0076194 A1 | 3/2011 | Kitagawa | |
| 2011/0076780 A1 | 3/2011 | Yamato | |
| 2011/0090066 A1 | 4/2011 | Yamaguchi et al. | |
| 2011/0091364 A1 | 4/2011 | Voit | |
| 2011/0095864 A1 | 4/2011 | Trueeb et al. | |
| 2011/0123416 A1 | 5/2011 | Giraud | |
| 2011/0143947 A1 | 6/2011 | Chamberlin | |
| 2011/0158850 A1 | 6/2011 | Pedrazzini | |
| 2011/0189051 A1 | 8/2011 | Gelin | |
| 2011/0197661 A1 | 8/2011 | Riggenmann | |
| 2011/0200500 A1 | 8/2011 | Feilders | |
| 2011/0229374 A1 | 9/2011 | Tokunaga | |
| 2011/0232372 A1 | 9/2011 | Tokunaga | |
| 2011/0236259 A1 | 9/2011 | Mototsu | |
| 2011/0243792 A1 | 10/2011 | Tatsutani | |
| 2011/0256022 A1 | 10/2011 | Akutsu | |
| 2012/0028847 A1 | 2/2012 | Indermuhle | |

FOREIGN PATENT DOCUMENTS

| | | | |
|---|---|---|---|
| CA | 2502656 | 2/2004 | |
| CA | 2693321 | 2/2004 | |
| DE | 102007031117 | 1/2008 | |
| DE | 102007012524 | 9/2008 | |
| EP | 0036566 | 9/1984 | |
| EP | 0564970 | 10/1993 | |
| EP | 0577343 | 1/1994 | |
| EP | 0622305 | 11/1994 | |
| EP | 0631816 | 1/1995 | |
| EP | 0651254 | 5/1995 | |
| EP | 0467284 | 6/1995 | |
| EP | 0692308 | 1/1996 | |
| EP | 0694334 | 1/1996 | |
| EP | 0866335 | 9/1998 | |
| EP | 0734963 | 11/1998 | |
| EP | 0884104 | 12/1998 | |
| EP | 0909584 | 4/1999 | |
| EP | 0920915 | 6/1999 | |
| EP | 0738541 | 1/2002 | |
| EP | 0757253 | 4/2003 | |
| EP | 1122181 | 5/2003 | |
| EP | 1546009 | 2/2004 | |
| EP | 1546736 | 2/2004 | |
| EP | 0968766 | 9/2004 | |
| EP | 1216754 | 11/2004 | |
| EP | 0977037 | 8/2005 | |
| EP | 1566216 | 8/2005 | |
| EP | 1424291 | 3/2006 | |
| EP | 1655071 | 5/2006 | |
| EP | 1452869 | 11/2006 | |
| EP | 1739406 | 1/2007 | |
| EP | 1741488 | 1/2007 | |
| EP | 1231472 | 1/2008 | |
| EP | 1550498 | 7/2008 | |
| EP | 1767949 | 10/2008 | |
| EP | 1832880 | 10/2009 | |
| EP | 1546680 | 3/2011 | |
| EP | 2074431 | 4/2011 | |
| GB | 2354841 | 4/2001 | |
| JP | 8026461 | 1/1996 | |
| JP | 09166599 | 6/1997 | |
| JP | 09304397 | 11/1997 | |
| JP | 2000019182 | 1/2000 | |
| JP | 2000162215 | 6/2000 | |
| JP | 2001253530 | 9/2001 | |
| JP | 2003083987 | 3/2003 | |
| JP | 2007527011 | 9/2007 | |
| JP | 2008073653 | 4/2008 | |
| JP | 2010085125 | 4/2010 | |
| WO | 9320441 A1 | 10/1993 | |
| WO | WO 9320441 A1 * | 10/1993 | ............... B01L 3/08 |
| WO | WO9409352 | 4/1994 | |
| WO | WO9511083 | 4/1995 | |
| WO | WO9621851 | 7/1996 | |
| WO | WO9705492 | 2/1997 | |
| WO | WO9716734 | 5/1997 | |
| WO | WO9803264 | 1/1998 | |
| WO | WO9809579 | 3/1998 | |
| WO | WO9821594 | 5/1998 | |
| WO | WO9858262 | 12/1998 | |
| WO | WO9945360 | 9/1999 | |
| WO | WO9951718 | 10/1999 | |
| WO | WO9952634 | 10/1999 | |
| WO | WO0029114 | 5/2000 | |
| WO | WO0117682 | 3/2001 | |
| WO | WO0245648 | 6/2002 | |
| WO | WO03000420 | 1/2003 | |
| WO | WO03020427 | 3/2003 | |
| WO | WO2004013615 | 2/2004 | |
| WO | WO2004013639 | 2/2004 | |
| WO | WO2004013709 | 2/2004 | |
| WO | WO2004013710 | 2/2004 | |
| WO | WO2006021648 | 3/2006 | |
| WO | WO2007134066 | 11/2007 | |
| WO | WO2008113352 | 9/2008 | |
| WO | WO2009012808 | 1/2009 | |
| WO | WO2009024560 | 2/2009 | |
| WO | WO2009115760 | 9/2009 | |
| WO | WO2009144381 | 12/2009 | |
| WO | WO2009149324 | 12/2009 | |
| WO | WO2010132885 | 11/2010 | |
| WO | WO2011139888 | 11/2011 | |
| WO | WO2012057548 | 5/2012 | |

* cited by examiner

LINEAR TRACK DIAGNOSTIC ANALYZER

CROSS-REFERENCE TO RELATED APPLICATIONS

This application claims benefit of priority to U.S. provisional application No. 61/790,599, filed on Mar. 15, 2013, which is incorporated by reference in its entirety.

FIELD OF THE DISCLOSURE

This disclosure relates to a linear track of a diagnostic analyzer. The linear track has a pre-treatment lane which allows blood samples disposed within the pre-treatment lane to be pre-treated simultaneously as diagnostic testing is conducted on blood samples disposed within one or more parallel processing lanes. This increases through-put of the diagnostic analyzer.

BACKGROUND

Diagnostic analyzers are used to conduct testing on blood samples to determine a characteristic, trait, property, or condition of the blood samples. Diagnostic analyzers often utilize moving circular carousels which hold reaction vessels into which blood samples and reagents are added. In order to pre-treat the blood samples needing incubation time prior to diagnostically testing these blood samples, the circular carousels typically rotate around multiple times while the blood samples within the circular carousels are incubating. This increases the time duration of completing the analysis because the diagnostic analyzer has to wait until the circular carousels finish the pre-treatment cycles before diagnostically testing the pre-treated blood samples. Alternatively, a segment of a circular carousel may be used for a pretreatment incubation then transferred back to the first incubation entry point to continue processing. This decreases through-put because new blood samples are delayed to allow pre-treatment samples in process to continue. Moreover, use of the circular carousels requires a great deal of space, and requires that spots on the circular carousels be reserved for pre-treatment.

A diagnostic analyzer and method of testing a blood sample is needed to overcome one or more of the issues of one or more of the existing diagnostic analyzers.

SUMMARY

In one embodiment, a diagnostic analyzer system is disclosed. The diagnostic analyzer system includes a primary process lane, a pretreatment process lane, and a transferring device. The primary process lane includes: a plurality of movable reaction vessels for carrying out diagnostic testing on samples in the plurality of movable reaction vessels; a mixer for agitating the samples in the plurality of movable reaction vessels; and a diagnostic reaction optical detection unit in light communication with one of the samples in one of the plurality of movable reaction vessels. The pretreatment process lane includes a second plurality of movable reaction vessels operable to incubate, within the second plurality of movable reaction vessels, samples containing reagent to form pretreated samples with at least a portion of the pretreatment lane not being coextensive with the primary process lane. The transferring device is for transferring the pretreated samples from the pretreatment process lane to the primary process lane.

In another embodiment, a diagnostic analyzer system is disclosed. The diagnostic analyzer system includes a linear track, at least one pipetting device, and at least one diagnostic module. The linear track includes a pre-treatment lane disposed parallel to at least one processing lane. The linear track is for moving reaction vessels, containing samples, held by the pre-treatment lane and by the at least one processing lane. The pre-treatment lane is for pre-treating the samples in the reaction vessels in the pre-treatment lane. The pre-treatment lane is not connected to any diagnostic module for testing the samples in the reaction vessels in the pre-treatment lane. The at least one pipetting device is for transferring the pre-treated samples from the reaction vessels in the pre-treatment lane to the reaction vessels in the at least one processing lane. The at least one diagnostic module is connected to the at least one processing lane for testing the pre-treated samples transferred into the reaction vessels in the at least one processing lane.

In another embodiment, another diagnostic analyzer system is disclosed. The diagnostic analyzer system includes a linear track, sample pipetting devices, reagent pipetting devices, and at least one diagnostic module. The linear track includes processing lanes and a pre-treatment lane parallel to the processing lanes. The linear track is for moving reaction vessels, containing samples, held by the processing lanes and the pre-treatment lane. The sample pipetting devices are for pipetting the samples into the reaction vessels of each of the respective processing lanes and the pre-treatment lane. The reagent pipetting devices are each dedicated to a different one of the respective processing lanes and the pre-treatment lane for pipetting reagents into the reaction vessels of each of the respective processing lanes and the pre-treatment lane. The pre-treatment lane is for incubating the samples containing the pipetted reagents in the reaction vessels in the pre-treatment lane. The pre-treatment lane is not connected to any diagnostic module for testing the incubated samples containing the pipetted reagents in the reaction vessels in the pre-treatment lane. One of the sample pipetting devices is also for transferring the incubated samples containing the pipetted reagents from the reaction vessels in the pre-treatment lane to the reaction vessels in the processing lanes. The at least one diagnostic module is connected to the processing lanes for testing the incubated samples, containing the pipetted reagents, transferred into the reaction vessels in the processing lanes.

In still another embodiment, a method of testing a sample using a diagnostic analyzer is disclosed. In one step, a linear track, comprising a pre-treatment lane and at least one parallel processing lane, is moved thereby moving reaction vessels containing samples held by the pre-treatment lane and by the at least one parallel processing lane. In another step, the samples in the reaction vessels of the pre-treatment lane are pre-treated without diagnostically testing them. In an additional step, the pre-treated samples are pipetted from the reaction vessels in the pre-treatment lane to the reaction vessels in the at least one parallel processing lane. In yet another step, the pipetted pre-treated samples in the reaction vessels of the at least one parallel processing lane are diagnostically tested.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
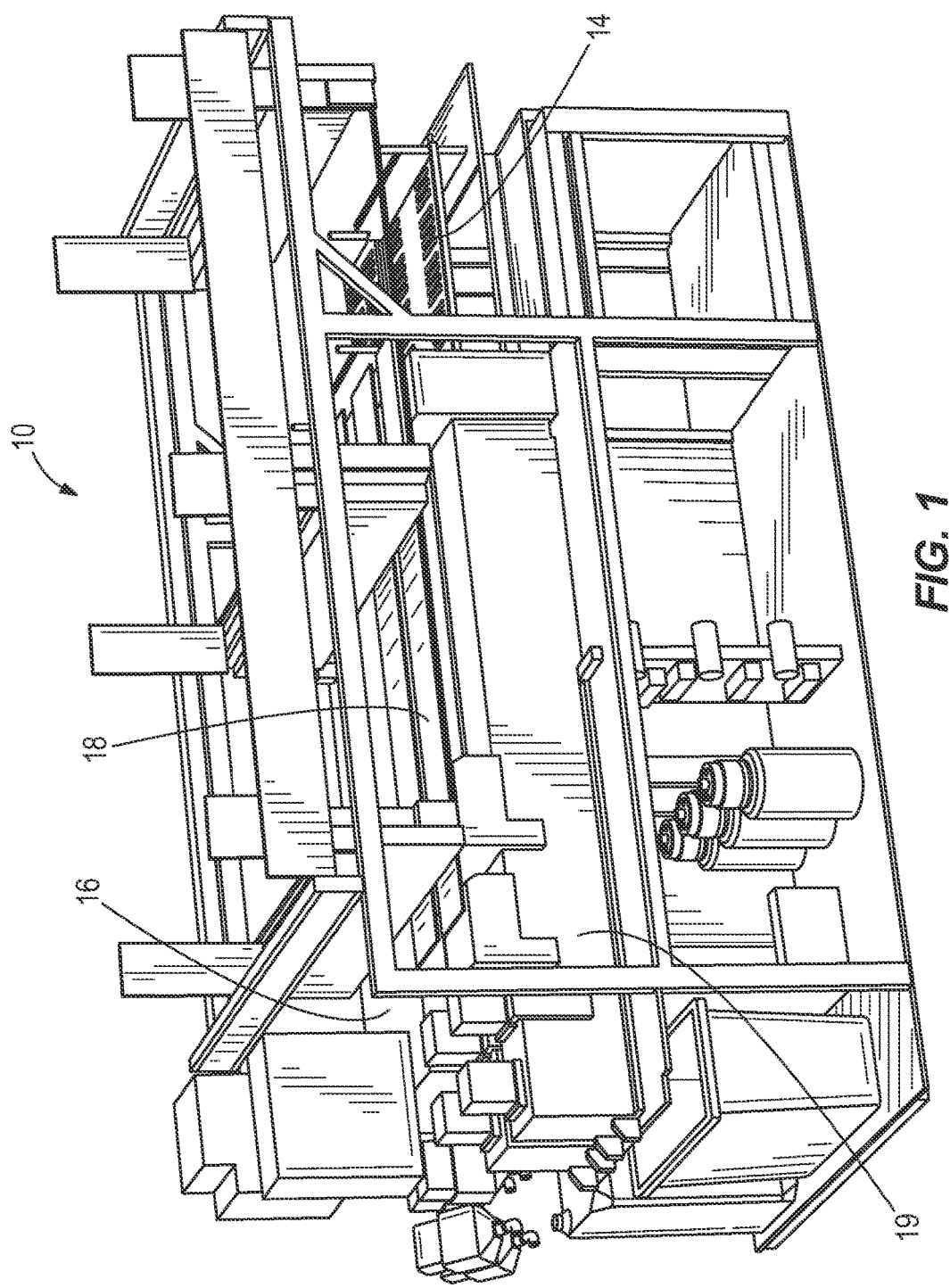
FIG. 1 illustrates a perspective view of one embodiment of a diagnostic analyzer system.
Figure 2:
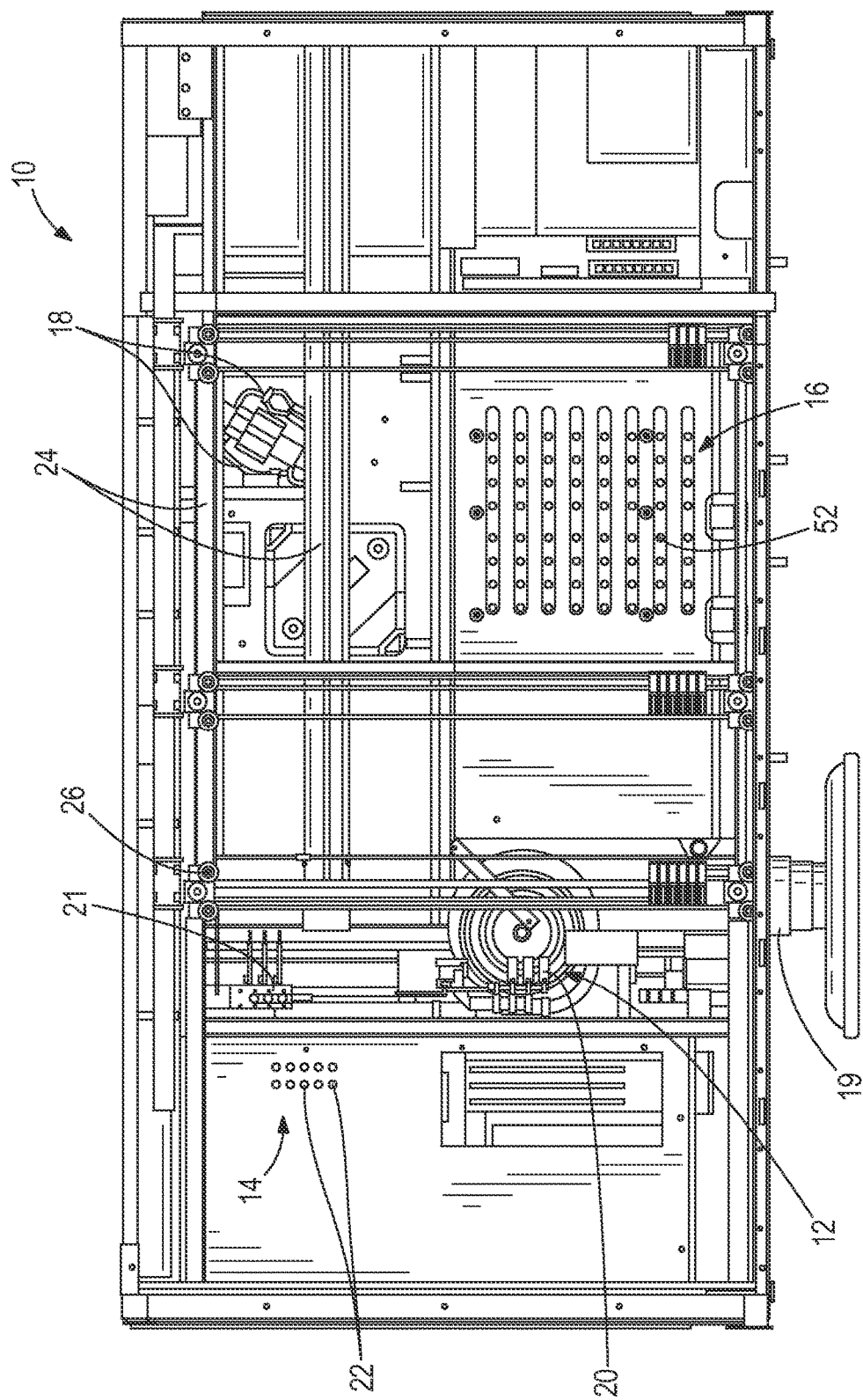
FIG. 2 illustrates a top view of the diagnostic analyzer system of FIG. 1.

FIGS. 1 and 2 respectively illustrate a perspective view and a top view of one embodiment of a diagnostic analyzer system 10. As shown collectively in FIGS. 1 and 2, the diagnostic analyzer system 10 comprises a reaction vessel loading zone 12, a sample storage zone 14, a reagent storage zone 16, a testing zone 18, and one or more processors 19. The one or more processors 19 may control the actions of the diagnostic analyzer system 10. The reaction vessel loading zone 12 comprises a zone which supplies reaction vessels 20 to the testing zone 18 preferably using a robot 21. The sample storage zone 14 comprises a zone which supplies samples 22 to the testing zone 18 for testing. The samples 22 comprise blood samples, and may include other body fluid sample. The samples may be taken from a mammal, a human, an animal, or any type of living creature. The reagent storage zone 16 comprises a zone which supplies reagents 24 to the testing zone 18. The testing zone 18 comprises a zone which conducts testing on the samples 22 to determine a measurement, a property, a trait, or a condition of the samples 22. In one embodiment, shown if FIG. 2, the testing zone 18 comprises two linear tracks 24. In other embodiments, the testing zone 18 may comprise any number of linear tracks 24. In one embodiment, the linear tracks 24 are made of stainless steel; however, other suitable materials may be used. Preferably, the linear tracks 24 and the entire assemblies are conductive to eliminate a build-up of static electricity. In the preferred embodiment, shown in FIG. 2, the linear tracks 24 are substantially identical. In other embodiments, the linear tracks 24 may vary. Motor 26 provides power for translating or otherwise moving the linear tracks 24 in the direction of a processing path. In other embodiments, any number of motors 26 may be used to provide power for translating or otherwise moving the linear tracks 24.

Figure 3:
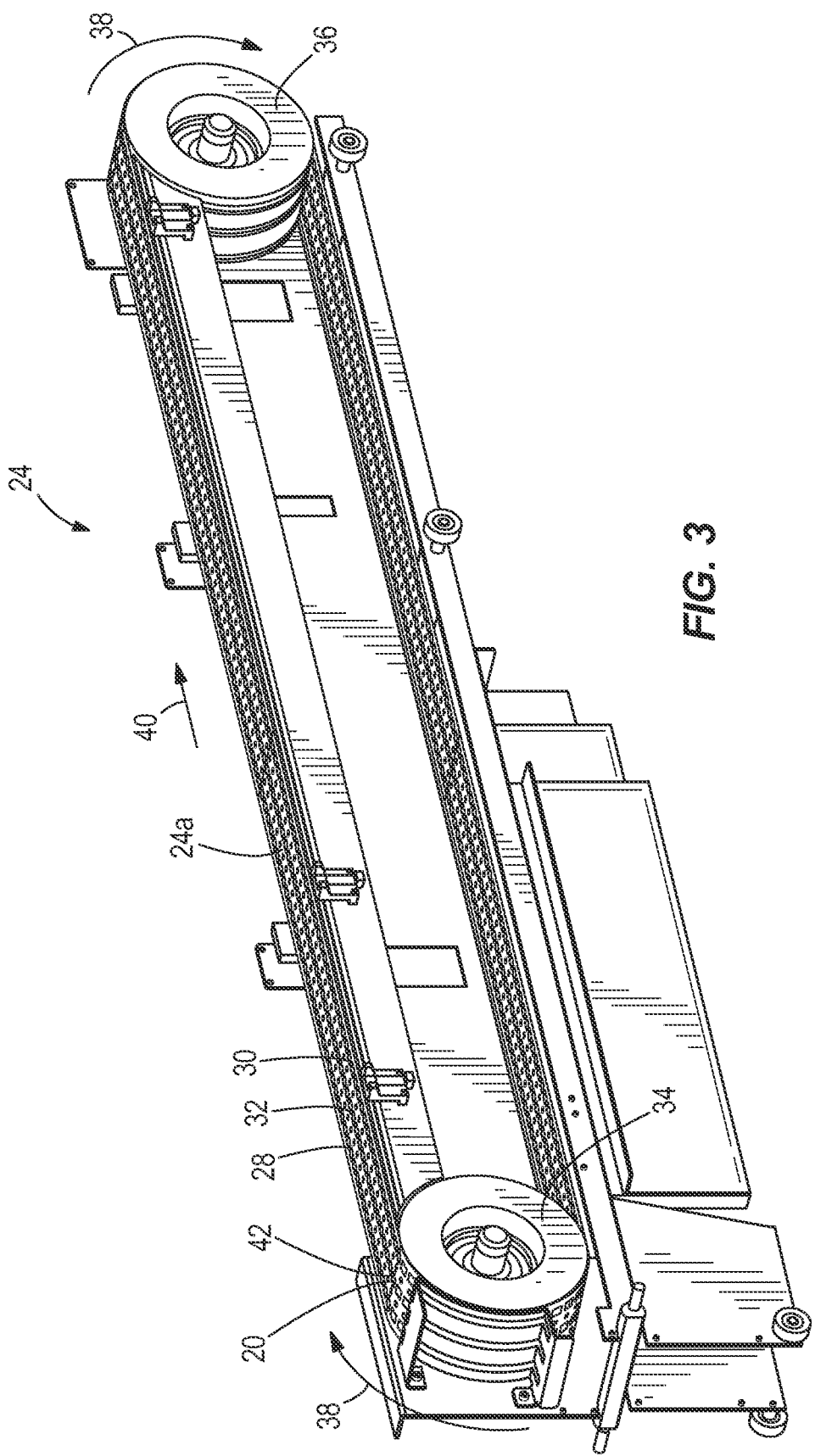
FIG. 3 illustrates a perspective view of a linear track removed from the diagnostic analyzer system of FIG. 1.

FIG. 3 illustrates a perspective view of one of a portion of the testing zone, and in particular, the linear tracks 24 of FIGS. 1 and 2 removed from the diagnostic analyzer system 10. In the embodiment of FIG. 3, the linear track 24 comprises two outer processing lanes 28 and 30, and a pre-treatment lane 32 which is disposed between and parallel to the two outer processing lanes 28 and 30. As discussed in more detail below, the outer processing lanes 28 and 30 are used to conduct diagnostic tests on samples. In other embodiments, the linear track 24 may comprise any number of processing and pre-treatment lanes in varied configurations. In the embodiment of FIG. 3, the linear track 24 is formed as a continuous linear belt-like track that is disposed around pulleys 34 and 36. Pulleys 34 and 36 may engage the linear track 24 in a sprocket-wheel engagement, in a friction engagement, or other forms of engagement to cause translation or movement of the linear track 24. The motor 26 of FIG. 2 supplies power to one or more of the pulleys 34 and 36 of FIG. 3 in order to rotate the pulleys 34 and 36 in the clockwise direction 38. The rotation of the pulleys 34 and 36 causes the attached linear track 24 to rotate with and around the pulleys 34 and 36 in the clockwise direction 38 thereby moving the outer processing lanes 28 and 30 and the pre-treatment lane 32 of the linear track 24 simultaneously. In the embodiment of FIG. 3, the processing lanes 28, 30 and pre-treatment lane 32 are defined by a plurality of longitudinal openings or slots 42 within the linear track 24, the slots 42 for accommodating a plurality of reaction vessels. As a top portion 24a of the linear track 24 moves in linear direction 40 due to the rotation of the pulleys 34 and 36, the reaction vessels 20 held in place within the plurality of slots 42 of the linear track 24 also move in linear direction 40. Preferably, the plurality of slots 42 are precision laser-cut slots of the linear track 24. The processing lanes 28, 30 and pre-treatment lane 32 may also be defined by a plurality of reaction vessel holders attached to the linear track as well as other manners to engage a reaction vessel to a linear track to cause motion of the reaction vessels. Further, although the embodiment of FIG. 3 depicts simultaneous movement of the reaction vessels in the pretreatment and processing lanes via a single mechanism for translation or movement of the entire linear track, the lanes can be separated in to different tracks and moved by different mechanisms and at different rates in other embodiments.

Figure 4:
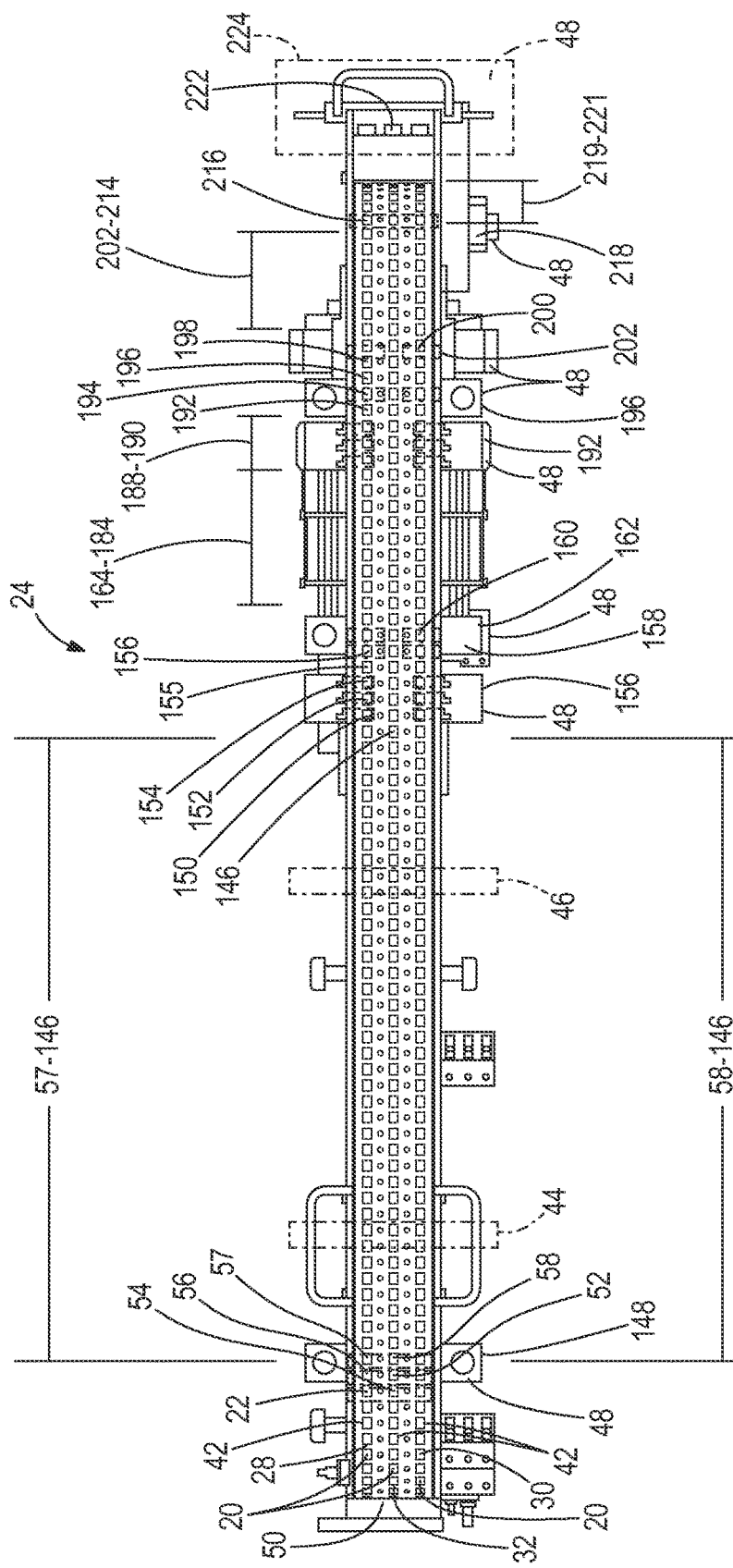
FIG. 4 illustrates a top view of the linear track of FIG. 3 and further shows at least one sample pipettor, at least one reagent pipettor, and a plurality of modules connected to the linear track.

FIG. 4 illustrates a top view of the linear track 24 of FIG. 3 and further shows at least one sample pipettor 44, at least one reagent pipettor 46, and a plurality of modules 48 adjacent to the linear track 24. Each of the two outer processing lanes 28 and 30 and the pre-treatment lane 32 comprise the plurality of slots 42 disposed in the linear track 24. The slots 42 within the outer processing lanes 28 and 30 and the pre-treatment lane 32 are each precisely sized to receive and hold one of the reaction vessels 20 from the loading zone 12 of FIG. 2. In the embodiment of FIG. 4, both the slots 42 and the reaction vessels 20 are rectangular. In other embodiments, the slots 42 and the reaction vessels 20 may comprise varying shapes and sizes. The loading zone 12 loads the reaction vessels 20 into the slots 42 of the outer processing lanes 28 and 30 and the pre-treatment lane 32 when the slots 42 are located at location 50 as the linear track 24 incrementally rotates around the pulleys 34 and 36 of FIG. 3. Preferably, location 50 is located at the center of the curved portion of the track 24 as it curves around pulley 34. There is a delay of twenty-four seconds each time the track 24 rotates into a new location to allow the loading zone 12 of FIG. 2 to have time to load the reaction vessels 20 into the slots of the outer processing lanes 28 and 30 and the pre-treatment lane 32. In other embodiments, the loading zone 12 may load the reaction vessels 20 into the slots 42 of the outer processing lanes 28 and 30 and the pre-treatment lane 32 when the slots 42 are located at varying locations as the linear track 24 rotates around the pulleys 34 and 36. In additional embodiments the incremental delay at each of the locations, as the track 24 rotates into new positions, referenced throughout this disclosure may further vary in duration.

Figure 5:
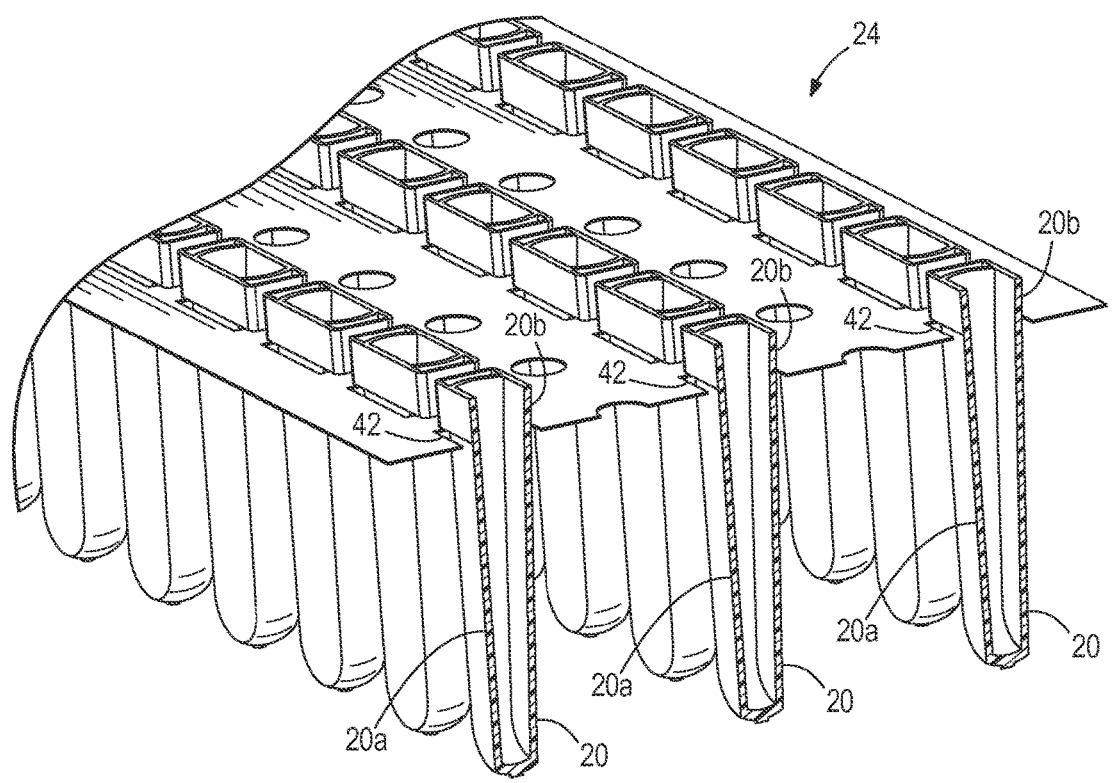
FIG. 5 illustrates a cross-section view of a portion of the linear track of FIG. 4 with reaction vessels held in place within slots of the linear track.

FIG. 5 illustrates a cross-section view of a portion of the linear track 24 of FIG. 4 with the reaction vessels 20 held in place within the slots 42 of the linear track 24. The slots 42 are sized so that the reaction vessels 20 may be inserted through the slots 42 so that a bottom portion 20a of the reaction vessels 20 extends out of and below the slots 42 and a top portion 20b of the reaction vessels 20 extends out of and above the slots 42.

Viewing FIG. 4, the pre-treatment lane 32 is used when a pre-treatment of samples with reagents is needed prior to primary processing (i.e. diagnostically testing) to allow the combination to undergo an additional incubation time other than the incubation time provided by the processing lanes 28 and 30. When pretreatment is required in this process, the at least one sample pipettor 44 pipettes samples 22 from the sample storage zone 14 of FIG. 2 into the reaction vessels 20 of FIG. 1 held in the slots 42 of the pre-treatment lane 32 at location 54 at the beginning of a twenty-four second cycle. Preferably, location 54 comprises the first spot where the track 24 levels off into a substantially horizontal position after curving around the pulley 34. In other embodiments, any number, type, or arrangement of sample pipetting devices may be used to pipette the samples 22 into the reaction vessels 20 held in the slots 42 of the pre-treatment lane 32 at any location.

Subsequently, the at least one reagent pipettor 46 pipettes reagents 52 from the reagent storage zone 16 of FIG. 2 into the samples 22 disposed in the reaction vessels 20 held in the slots 42 of the pre-treatment lane 32 when each of the slots 42 of the pre-treatment lane 32 increments, after the twenty-four second delay, to the next spot at location 56 as the linear track 24 continues to rotate around the pulleys 34 and 36 of FIG. 3 from location 54. In one embodiment, the reagents 52 dispensed at location 56 may comprise microparticles that are coated with antigen and diluent. In one embodiment, the at least one reagent pipettor 46 may comprise a plurality of reagent pipettors which are each dedicated to only one lane of the processing lanes 28 and 30 and the one or more pre-treatment lanes 32. In other embodiments, any number, type, or arrangement of reagent pipetting devices may be used to pipette the reagents 52 into the reaction vessels 20 held in the slots 42 of the processing lanes 28 and 30 at any location.

Next, in the embodiment of FIG. 4, the pre-treatment lane 32 continues to incrementally move, with the twenty-four second delay at each incremental location, to as many of the locations 58-146 as needed for the total amount of incubation time required for the particular pretreatment of the pre-treated samples 22 (which were combined with the reagents 52). After the reaction vessels 20 held in the slots 42 of the pre-treatment lane 32 incubate for the desired amount of incubation time (anywhere between location 58 to location 146 incrementing by 2 i.e. location 58, location 60, location 62 . . . location 146) required for the particular pre-treatment, the pre-treated samples 22 (which were combined with the reagents 52) will have incubated for anywhere from twenty-four seconds (1 twenty-four second delay cycle) to eighteen minutes (45 twenty-four second delay cycles) due to the twenty-four second delay cycles at each location. In one embodiment, during this period the antigen on the microparticles of the reagents 52 binds with the antibody in the samples 22. In other embodiments, the number of incubation locations and delays may vary. When the pre-treated samples 22 (which were combined with the reagents 52) have incubated for the appropriate additional amount of time in the pre-treatment lane 32 for the diagnostic test to be run, the pre-treated sample 22 is transferred to the primary processing lanes 28 and 30. In one embodiment, the at least one sample pipettor 44 transfers the pre-treated samples 22 from the reaction vessels 20 held in the slots 42 of the pre-treatment lane 32 at any of locations 58-146 (anywhere between location 58 to location 146 incrementing by 2 i.e. location 58, location 60, location 62 . . . location 146) to one or more of the reaction vessels 20 held in the slots 42 of the processing lanes 28 and 30 at location 54. In other embodiments, any number, type, or arrangement of pipetting devices may be used to transfer the pre-treated samples 22 from the reaction vessels 20 held in the slots 42 of the pre-treatment lane 32 at any location to one or more reaction vessels 20 held in the slots 42 of the processing lanes 28 and 30 at any location. In another embodiment, the reaction vessel 20 in the pre-treatment lane 32 may be transferred to one of the primary processing lanes 28 and 30.

While the incubation of the pre-treated samples 22 is being done in the pre-treatment lane 32, the processing lanes 28 and 30 simultaneously process (i.e. diagnostically test) samples 22 (which may or may not have been pre-treated in the pre-treatment lane 32) in the processing lanes 28 and 30. In such manner, use of the pre-treatment lane 32 significantly increases the throughput of the diagnostic analyzer system 10 while reducing the space needed for running pre-treatments on the samples 22 due to the pre-treatment lane 32 being disposed on the same track 24 but substantially separate from the processing lanes 28 and 30 such that at least a portion of the pretreatment lane 32 is not cooextensive with the primary processing lanes 28 and 30. In the embodiment of FIG. 4, parallel, closely located pretreatment and processing lanes provide increased throughput.

It is noted that, in one preferred embodiment, no processing (i.e. diagnostic testing) of the samples 22 takes place in the pre-treatment lane 32. No diagnostic modules are connected to the pre-treatment lane 32 for testing the samples 22 in the pre-treatment lane 32. The samples 22 in the pre-treatment lane 32 only have reagents 52 added to them and then incubate prior to being transferred to the processing lanes 28 and 30 without anything further being done to the samples 22 in the pre-treatment lane 32 (i.e. no treatments, processes, or diagnostic testing).

When a pre-treatment of samples 22 with reagents 52 is not needed prior to processing (i.e. the incubation time provided by the processing lanes 28 and 30 is sufficient for diagnostically testing the samples 22 in the processing lanes 28 and 30 without needing the additional incubation time provided by the pre-treatment lane 32), the at least one sample pipettor 44 pipettes the samples 22 from the sample storage zone 14 of FIG. 2 into the reaction vessels 20 held in the slots 42 of the processing lanes 28 and 30 when each of the slots 42 of the processing lanes 28 and 30 increments, after the twenty-four second delay, to location 54 as the linear track 24 incrementally rotates around the pulleys 34 and 36 of FIG. 3 from location 50. In other embodiments, any number, type, or arrangement of sample pipetting devices may be used to pipette the samples 22 into the reaction vessels 20 held in the slots 42 of the processing lanes 28 and 30 at any location. Moreover, the time delay may vary.

Subsequently, the at least one reagent pipettor 46 pipettes the reagents 52 from the reagent storage zone 16 of FIG. 2 into the samples 22 disposed in the reaction vessels 20 held in the slots 42 of the processing lanes 28 and 30 when each of the slots 42 of the processing lanes 28 and 30 increments, after the twenty-four second delay, to location 56 as the linear track 24 continues to rotate around the pulleys 34 and 36 of FIG. 3 from location 54. In other embodiments, any number, type, arrangement, or assignment of pipetting devices may be used to pipette the reagents 52 into the samples 22 disposed in the reaction vessels 20 held in the slots 42 of the processing lanes 28 and 30 at any location.

Next, the primary processing lanes 28 and 30 continue to incrementally move, after the twenty-four second delay, to location 57. At location 57, the samples 22 and reagents 52 contained within the reaction vessels 20 held in the slots 42 of the processing lanes 28 and 30 are mixed together with mixing module 148. It is noted that the mixing module 148 in FIG. 4 is not connected to the pre-treatment lane 32. Next, the mixed samples 22 and reagents 52 within the reaction vessels 20 held in the slots 42 of the processing lanes 28 and 30 are moved incrementally, with the twenty-four second delay at each location, from location 57 to location 146 (i.e. 57, 58, 60, 62, 64 . . . 146) stopping at every location between location 57 and location 146 during which the mixture incubates. In one embodiment, during this period, antigen on the microparticles of the reagents 52 binds with the antibody in the samples 22. In other embodiments, the types of reactions, the number of incubation locations and delays may vary.

Subsequently, the incubated mixed samples 22 and reagents 52 within the reaction vessels 20 held in the slots 42 of the processing lanes 28 and 38 are moved incrementally, with the twenty-four second delay at each location, from location 146 to locations 150, 152, and 154. At locations 150, 152, and 154, the incubated mixed samples 22 and reagents 52 within the reaction vessels 20 held in the slots 42 of the processing lanes 28 and 30 are washed with washing module 156. During the washing, unbound materials of the reagents 52 are washed away from the samples 22. The washing module 156 comprises at least one actuated magnet and at least one washing pipette which allows the washing module 156 to selectively actuate the magnet and use the at least one washing pipette to wash only the selected incubated samples 22 and reagents 52 within the reaction vessels 20 held in the slots 42 of the processing lanes 28 and 30. In such manner, the non-selected incubated samples 22 and reagents 52 within the reaction vessels 20 can pass by without washing. It is noted that, in the embodiment of FIG. 4, the washing module 156 is not connected to the pre-treatment lane 32.

Next, the washed samples 22 in the reaction vessels 20 held in the slots 42 of the processing lanes 28 and 30 are moved incrementally, with the twenty-four second delay at each location, from location 154 to location 155 and then to location 156. At location 156, a conjugate dispensing module 158 dispenses conjugate into the samples 22 in the reaction vessels 20 held in the slots 42 of the processing lanes 28 and 30. It is noted that, in the embodiment of FIG. 4, the conjugate dispensing module 158 is not connected to the pre-treatment lane 32. The samples 22 with the dispensed conjugate held in the reaction vessels 20 held in the slots 42 of the processing lanes 28 and 30 are then moved incrementally, after the twenty-four second delay, to location 160. At location 160 another mixing module 162 mixes the samples 22 with the dispensed conjugate in the reaction vessels 20 held in the slots 42 of the processing lanes 28 and 30. It is noted that the mixing module 162 is not connected to the pre-treatment lane 32.

After another twenty-four second delay, the mixed samples 22 with the dispensed conjugate in the reaction vessels 20 held in the slots 42 of the processing lanes 28 and 30 incrementally move, after the twenty-four second delay at each location, to each of locations 164-184 (stopping at every location between location 164 and location 184 i.e. 164, 166, 168, . . . 184) during which time-period the mixed samples 22 with the dispensed conjugate in the reaction vessels 20 held in the slots 42 of the processing lanes 28 and 30 incubate. When the reaction vessels 20 held in the slots 42 of the processing lanes 28 and 30 reach location 184 and undergo the twenty-four second delay at that location, the mixed samples 22 with the dispensed conjugate in the reaction vessels 20 held in the slots 42 of the processing lanes 28 and 30 will have incubated for four minutes due to the forty-five twenty-four second incremental delays. During this incubation period, the conjugate binds with any immune complex bound to the microparticles. In other embodiments, the number of incubation locations and delays may vary.

Next, the incubated samples 22 in the reaction vessels 20 held in the slots 42 of the processing lanes 28 and 30 incrementally move, after the twenty-four second delay at each location, to each of locations 186, 188, and 190. Another washing module 192 at locations 186, 188, and 190 washes away unbound conjugate from the incubated samples 22.

Subsequently, the washed samples 22 in the reaction vessels 20 held in the slots 42 of the processing lanes 28 and 30 incrementally move through location 192 to location 194 undergoing the twenty-four second delay at each location. At location 194, a pre-trigger dispensing and mixing module 196 dispenses pre-trigger solution into the washed samples 22 in the reaction vessels 20 held in the slots 42 of the processing lanes 28 and 30 and then mixes the combination. It is noted that the pre-trigger dispensing and mixing module 196 is not connected to the pre-treatment lane 32, in the embodiment of FIG. 4.

Next, the mixed samples 22 containing the pre-trigger solution in the reaction vessels 20 held in the slots 42 of the processing lanes 28 and 30 incrementally move through locations 196 and 198 to location 200 undergoing the twenty-four second delay at each location. At location 200, a trigger dispensing and reading module 202, which in part comprises a diagnostic module, dispenses a trigger solution into the samples 22 mixed with the pre-trigger solution in the reaction vessels 20 held in the slots 42 of the processing lanes 28 and 30 and then takes a reading. The diagnostic module is preferably an optic diagnostic testing module which takes an optical reading to determine a measurement, a property, a trait, or condition of the samples 22 based on the optical reading. In other embodiments, varying diagnostic modules, other than optical diagnostic testing modules, may be utilized to determine a measurement, a property, a trait, or a condition of the samples 22. It is noted that the trigger dispensing and reading 202 is not connected to the pre-treatment lane 32.

Then, the read samples 22 in the reaction vessels 20 held in the slots 42 of the processing lanes 28 and 30 incrementally move through locations 202-214 to location 216 undergoing the twenty-four second delay at each location. At location 216, a liquid waste aspiration module 218 aspirates liquid waste, comprising the read samples 22, from the reaction vessels 20 held in the slots 42 of the processing lanes 28 and 30. At location 216, the liquid waste aspiration module 218 further aspirates liquid waste, to the extent there is any if a pre-treatment was run, from the reaction vessels 20 held in the slots 42 of the pre-treatment lane 32.

The empty reaction vessels 20 held in the slots 42 of the processing lanes 28 and 30 and held in the slots 42 of the pre-treatment lane 32 then incrementally move through locations 219-221 to location 222 undergoing the twenty-four second delay at each location. At location 222, which is curved downward, the empty reaction vessels 20 fall out of the slots 42 of the processing lanes 28 and 30 and out of the slots 42 of the pre-treatment lane 32 into a reaction vessel disposal module 224 which disposes of the empty reaction vessels 20.

In other embodiments, the diagnostic analyzer system 10 may vary. For instance, one or more linear tracks 24 may comprise one or more varying pre-treatment lanes 32, one or more varying processing lanes 30 and 32, one or more varying slots 42, or one or more varying modules 48 having different functions. Moreover, the delay duration may vary as the one or more linear tracks 24 increment.

Figure 6:
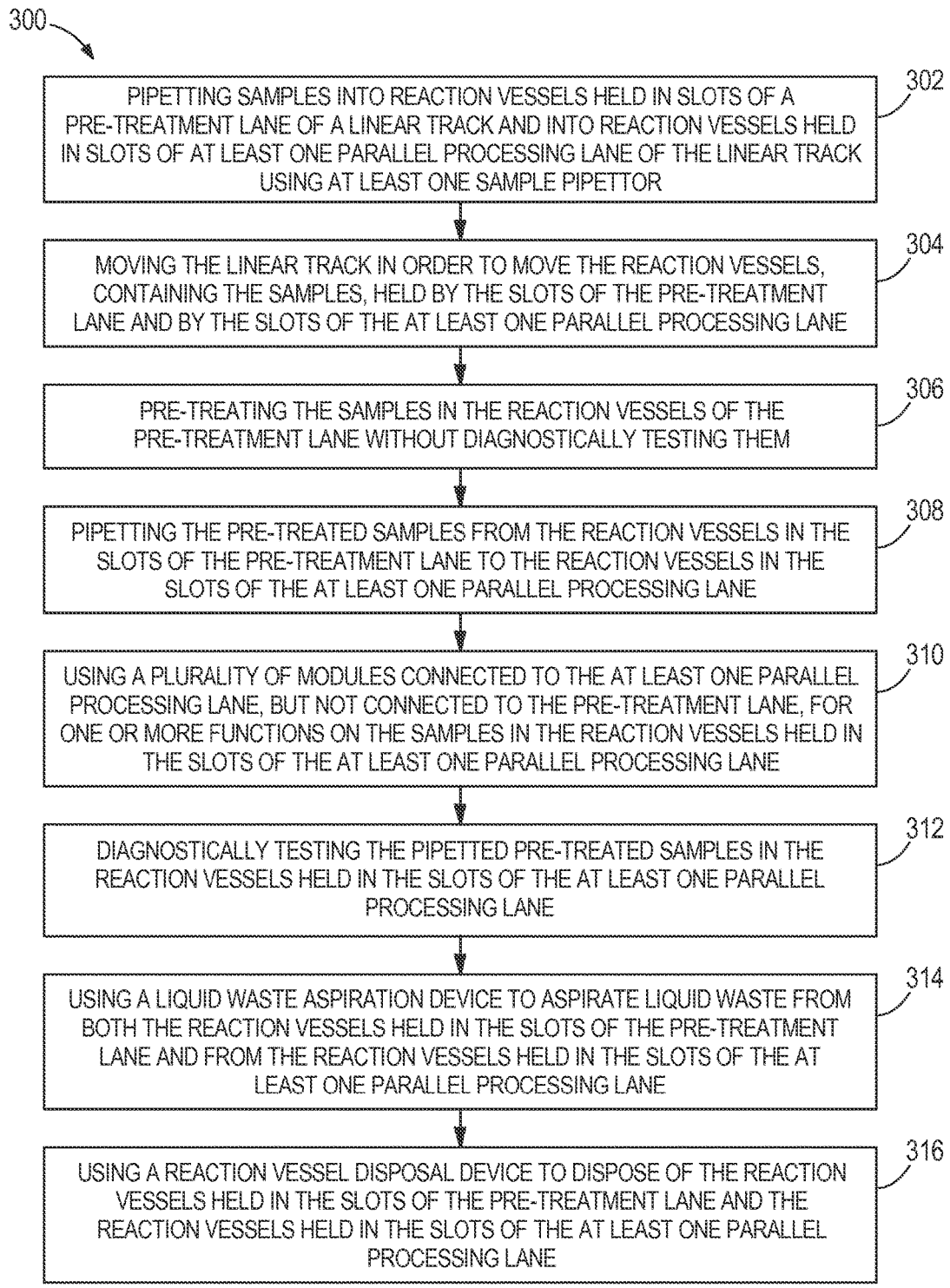
FIG. 6 is a flowchart illustrating one embodiment of a method of testing samples using a diagnostic analyzer.

FIG. 6 is a flowchart illustrating one embodiment of a method 300 of testing samples using a diagnostic analyzer. The method may utilize any of the embodiments of the diagnostic analyzer disclosed herein and may be controlled by one or more processors. In other embodiments, the method may utilize varying embodiments of the diagnostic analyzer. In step 302, samples may be pipetted into reaction vessels held in slots of a pre-treatment lane of a linear track and into reaction vessels held in slots of at least one parallel processing lane of the linear track using at least one sample pipettor. The pre-treatment lane may be disposed between and parallel to two parallel processing lanes. In step 304, the linear track may be moved in order to move the reaction vessels, containing the samples, held by the slots of the pre-treatment lane and by the slots of the at least one parallel processing lane. The pre-treatment lane and the at least one parallel processing lane may be moved in the same increments as the linear track moves.

In step 306, the samples in the reaction vessels of the pre-treatment lane may be pre-treated without diagnostically testing them. Step 306 may further comprise adding reagents to the samples held in the slots of the reaction vessels of the pre-treatment lane with at least one reagent pipettor when the linear track is disposed in one position. The at least one reagent pipettor may be dedicated to the pre-treatment lane. Step 306 may further comprise subsequently moving the linear track into advanced positions thereby incubating the samples, with the added reagents, in the reaction vessels held in the slots of the pre-treatment lane as the linear track moves. Step 306 may further comprise one or more additional reagent pipettors dedicated to the at least one parallel processing lane pipetting reagents into the samples held in the slots of the reaction vessels of the at least one parallel processing lane while the pre-treatment is occurring in the pre-treatment lane.

In step 308, the pre-treated samples may be pipetted from the reaction vessels in the slots of the pre-treatment lane to the reaction vessels in the slots of the at least one parallel processing lane. In step 310, a plurality of modules connected to the at least one parallel processing lane, but not connected to the pre-treatment lane, may be used for one or more functions on the samples in the reaction vessels held in the slots of the at least one parallel processing lane. The plurality of modules may not be used on the samples in the reaction vessels held in the slots of the pre-treatment lane. The plurality of modules may comprise a washing module, a conjugate dispensing module, a mixing module, a pre-trigger dispensing and mixing module, and a trigger dispensing module. In other embodiments, the plurality of modules may vary. Step 310 may further comprise washing some of the reaction vessels held by the slots of the at least one parallel processing lane by actuating at least one magnet and by using at least one washing pipette of the washing module. Step 310 may further comprise selectively not-washing other of the reaction vessels held by the slots of the at least one parallel processing lane by not actuating the at least one magnet and by not using the at least one washing pipette of the washing module.

In step 312, the pipetted pre-treated samples in the reaction vessels held in the slots of the at least one parallel processing lane may be diagnostically tested. Step 312 may further comprise testing the pipetted pre-treated samples in the reaction vessels held in the slots of the at least one parallel processing lane with an optical diagnostic module. In other embodiments, varying diagnostic modules may be used. In step 314, liquid waste may be aspirated from both the reaction vessels held in the slots of the pre-treatment lane and from the reaction vessels held in the slots of the at least one parallel processing lane using a liquid waste aspiration device. In step 316, the reaction vessels held in the slots of the pre-treatment lane and the reaction vessels held in the slots of the at least one parallel processing lane may be disposed of using a reaction vessel disposal device. In other embodiments, one or more steps of the method may be not-followed, may be modified in substance or chronology, or one or more additional steps may be added.

One or more embodiments of the disclosure may reduce one or more issues of one or more of the existing diagnostic analyzers. For instance, the linear path of the track creates a reliable and durable process path with a distinct beginning and end. This linear path allows for a better fit of the rectangular reaction vessels to prevent them from being scraped or caught on edges of the track. Two parallel processing lanes on each belt allows for increased throughput from parallel processing. The pre-treatment lane allows the throughput to be maintained with as much as half the tests needing one pre-treatment cycle. The assembly is conductive to minimize problems with static electricity. The pre-treatment lanes are connected to dedicated sample pipettors for transferring the pre-treated samples to the parallel processing lanes thereby avoiding interference with the parallel processing lane pipettors and further increasing through-put. The parallel processing lanes are connected to various modules for doing a variety of functions on the blood samples disposed within the reaction vessels carried by the parallel processing lanes. The various modules are not connected to the pre-treatment lane which avoids interference with the pre-treatment while allowing simultaneous diagnostic processing. The use of a washing zone actuated magnet with independently indexing washing pipettes allows samples to go directly through the wash zone, instead of having to go on a separate bypass path, without being washed. Common waste modules are utilized for both of the processing lanes and the pre-treatment lane in order to efficiently dispose of liquid waste and used reaction vessels. All of these improvements work to increase through-put and reduce space and cost of the diagnostic analyzer system.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the disclosure is defined by the appended claims. Accordingly, the disclosure is not to be restricted except in light of the appended claims and their equivalents.

The invention claimed is:

1. A method of testing using a diagnostic analyzer comprising:
   moving a linear track, comprising a pre-treatment lane and at least one parallel processing lane, thereby moving reaction vessels containing samples held by the pre-treatment lane and by the at least one parallel processing lane;
   pre-treating the samples in the reaction vessels of the pre-treatment lane without diagnostically testing them;
   pipetting the pre-treated samples from the reaction vessels in the pre-treatment lane to the reaction vessels in the at least one parallel processing lane; and
   subsequently diagnostically testing the pipetted pre-treated samples in the reaction vessels.

2. The method of claim 1 wherein the moving the linear track further comprises incrementing the pre-treatment lane and the at least one parallel processing lane in the same increments as the linear track moves.

3. The method of claim 1 wherein the pre-treating the samples in the reaction vessels of the pre-treatment lane further comprises adding reagents to the samples held in the reaction vessels of the pre-treatment lane when the linear track is disposed in one location, and subsequently moving the linear track into advanced locations thereby incubating the samples with the added reagents in the reaction vessels of the pre-treatment lane as the linear track moves.

4. The method of claim 1 wherein each of the pre-treatment lane and the at least one parallel processing lane comprise a plurality of slots in the linear track, and further comprising holding the reaction vessels within the plurality of slots.

5. The method of claim 1 further comprising pipetting the samples into the reaction vessels of the pre-treatment lane and into the reaction vessels of the at least one parallel processing lane using at least one sample pipettor.

6. The method of claim 1 further comprising pipetting reagents into the reaction vessels of the pre-treatment lane and into the reaction vessels of the at least one parallel processing lane using at least one reagent pipettor.

7. The method of claim 1 wherein the pre-treating the samples in the reaction vessels of the pre-treatment lane further comprises pipetting reagents into the reaction vessels of the pre-treatment lane using a reagent pipettor only dedicated to the pre-treatment lane.

8. The method of claim 1 further comprising pipetting reagents into the reaction vessels of the at least one parallel processing lane using at least one reagent pipettor only dedicated to the at least one parallel processing lane.

9. The method of claim 1 further comprising washing some of the reaction vessels of the at least one parallel processing lane by actuating at least one magnet, to bind materials contained in reagents in those reaction vessels, and by using at least one washing pipette, and further comprising selectively not-washing other of the reaction vessels of the at least one parallel processing lane by not actuating the at least one magnet, to not bind the materials contained in the reagents in those other reaction vessels, and by not using the at least one washing pipette.

* * * * *

UNITED STATES PATENT AND TRADEMARK OFFICE
CERTIFICATE OF CORRECTION

PATENT NO. : 9,632,103 B2
APPLICATION NO. : 14/213847
DATED : April 25, 2017
INVENTOR(S) : Joseph P. Donohue et al.

Page 1 of 1

It is certified that error appears in the above-identified patent and that said Letters Patent is hereby corrected as shown below:

On the Title Page

Please correct the inventor information as follows:
(72) Inventor: Please add -- Ryan Patrick Johnson, Bedford TX (US) --

Signed and Sealed this
Fourth Day of December, 2018

Andrei Iancu
*Director of the United States Patent and Trademark Office*